United States Patent [19]

Takemoto et al.

[11] 4,312,979

[45] Jan. 26, 1982

[54] POLYSACCHARIDES CONTAINING ALLOSE

[75] Inventors: Hisao Takemoto; Tatsuo Igarashi, both of Shin-Nanyo, Japan

[73] Assignee: Toyo Soda Manufacturing Co., Ltd., Tokyo, Japan

[21] Appl. No.: 30,444

[22] Filed: Apr. 16, 1979

[30] Foreign Application Priority Data

Apr. 20, 1978 [JP]  Japan ................................... 53-45918
Dec. 5, 1978 [JP]  Japan ................................... 53-149715

[51] Int. Cl.³ ............................................... C07H 1/08
[52] U.S. Cl. .......................................... 536/1; 435/72; 435/101; 536/114

[58] Field of Search .................... 536/1, 18, 114, 4; 435/101

[56] References Cited

U.S. PATENT DOCUMENTS 3,711,462  1/1973  Abdo et al. .............................. 536/1
4,186,025  1/1980  Kang et al. .............................. 536/1

*Primary Examiner*—Johnnie R. Brown
*Attorney, Agent, or Firm*—Scully, Scott, Murphy & Presser

[57] ABSTRACT

A new polysaccharide including allose as a constituent sugar and further characterized by galactose as a major constituent sugar is described. The polysaccharide is produced extracellularly by cultivation of *Pseudomonas viscogena* strains in nutrient medium.

6 Claims, 2 Drawing Figures

FIG. I

POLYSACCHARIDES CONTAINING ALLOSE

FIELD OF THE INVENTION

This invention relates to new and useful polysaccharides and the method of their preparation.

BACKGROUND OF THE INVENTION

Polysaccharides are generally classified according to their origin, i.e., from plants, animals and microorganisms. For example, plant polysaccharides include cellulose, pectin, amylose carrageenin, agar-agar and the like; animal, heparin and condroitin-sulfate; and microorganisms, dextrans, xanthan gum, pullan, curdlan and the like. Most such polysaccharides contain glucose as the principal constituent sugar. As is well known, many of the aforesaid polysaccharides are used in industry for many and varied purposes such as thickening agents, stabilizers for foams and the like, emulsifiers, and are widely used in the food, cosmetic and pharmaceutical industry. Polysaccharides can also be used as moldable materials for biodegradable films, as well as flocculating agents since they can be gelled in aqueous solution in the presence of calcium ion.

It is known that species of the genus Pseudomonas produce polysaccharides: Applied Microbiology, published December, 1974, p. 903; Japanese published application nos. 151392/76; 130594/76 and 21393/77. The main constituent sugar of the polysaccharides so produced is glucose.

SUMMARY OF THE INVENTION

This invention provides novel polysaccharides which are characterized by containing allose as a constituent sugar. Allose is an aldohexose which heretofore was not believed to occur naturally. In addition, the novel polysaccharides of this invention also contain galactose as the most prevailing constituent sugar. The sum of allose and galactose content is at 50% mol-percent with galactose being substantially predominant.

The new polysaccharides of this invention are produced by the process of cultivating certain new bacteria of the genus Pseudomonas in nutrient media to accumulate the polysaccharides in the medium from which the polysaccharides are eventually separated and recovered by known methods.

The new bacteria of the genus Pseudomonas for use in the present invention are those which are capable of accumulating extracellularly, i.e., in the fermentation medium, allose-containing polysaccharides. One such microorganism is *Pseudomonas viscogena,* isolated from the soil. The taxonomical characteristics of this organism are as follows:

(A) Study of Cell Morphology after inoculation at 30° C. for 6–24 hours on a nutrient broth agar:
  1. Cell form: rods
  2. Cell size: 1.0×0.7 (μ)
  3. Arrangement: single or pair
  4. Motility: motile by polar flagella
  5. Endspore: none
  6. Gram stainity: negative
  7. Acid-fast: negative (B) Cultural Characteristics:
  1. Cultivation on a nutrient broth agar plate after inoculation at 30° C. for 2 days;
    (a) Rate for colony formation: usual
    (b) Form of colonies: circular, about 3.5 mm in diameter
    (c) Surface of colonies: smooth
    (d) Elevation of Growth: convex
    (e) Edge of colonies: entire
    (f) Content of colonies: amorphous
    (g) Tint of colonies: pale yellow
    (h) Transmittance of colonies: opaque
    (i) Glistening of colonies: glistning
    (j) Formation of soluble coloring material: none
  2. Cultivation on a nutrient broth agar slant after inoculation at 30° C. for 2 days;
    (a) Growth: abundant growth
    (b) Form of growth: spreading
    (c) Gross-sectional Elevation of colonies: flat
    (d) Glistening of growth: glistening
    (e) Surface of colonies: smooth
    (f) Transmittance of colonies: opaque
    (g) Tint of colonies: pale yellow
    (h) Rheological characteristics of colonies: viscid
  3. Cultivation in a nutrient broth after inoculation at 30° C. for 2 days;
    (a) Growth on surface: membranous
    (b) Turbidity: moderately turbid
    (c) Precipitate formation: compact
    (d) Generation of gas: none
    (e) Coloration of medium: none
  4. Cultivation in a nutrient broth agar stab after inoculation at 30° C. for 2 days;
    (a) Location of growth: best at top
    (b) Line of puncture: pappilate
  5. Cultivation in a nutrient broth gelatin stab after inoculation at 20° C. for 2 weeks;
    (a) Liquification of gelatin: none
  6. Growth in milk
    (a) Reaction: decolorization
    (b) Gas formation: none
    (c) Coagulation or liquification: coagulation (C) Physiological Characteristics:
  1. Reduction of nitrate: Reduction to $N_2$ occurs.
  2. Denitrification: —
  3. MR test: +
  4. VP test: +
  5. Formation of indole: +
  6. Formation of hydrogen sulfide: +
  7. Hydrolysis of starch: —
  8. Utilization of citric acid: —
  9. Utilization of inorganic nitrogen source: Nitrogen source in either $NO_3$ or $NH_3$-form is utilized.
  10. Formation of coloring material: Green fluorescent material is formed.
  11. Ulease: +
  12. Oxidase: +
  13. Catalase: +
  14. Range for growth: 4–10 in pH and at a temperature of 10°–42° C.
  15. Oxygen requirement: aerobic
  O-F test: oxidation
  17. Acid or gas formation from sugars;

| Sugar | Growth | Acid | Gas |
|---|---|---|---|
| L-Arabinose | + | + | — |
| D-Xylose | + | + | — |
| D-Glucose | + | (+) | — |
| D-Mannose | + | — | — |
| D-Fructose | + | + | — |
| D-Galactose | + | + | — |
| Maltose | + | — | — |

-continued

| Sugar | Growth | Acid | Gas |
|---|---|---|---|
| Sucrose | + | − | − |
| Lactose | + | − | − |
| Threpharose | + | − | − |
| D-Sorbit | + | − | − |
| D-Mannit | + | − | − |
| Inosit | + | − | − |
| Glycerine | + | + | − |
| Starch | + | − | − |

Taxonomical identification according to Bergey's Manual of Determinative Bacteriology, 8th Edition (1974) shows that the microorganism has characteristics of genus Pseudomonas. However, no known species in the genus has been found having identification features which coincide with those of the newly found microorganism. Accordingly, this new species has been given the name, Pseudomonas viscogena.

A typical strain of the species, Pseudomonas viscogena TS-1004 is deposited at the Fermentation Research Institute (Tokyo, Japan) under accession number Ferm-P No. 3811 and also at the American Type Culture Collection under accession number ATCC 31504.

Pseudomonas viscogena can be cultivated aerobically in a nutrient medium comprising a carbon source, nitrogen source, and salts, as well as optional growth promoters.

Carbon sources include, for example, various hydroxy-containing organic compounds, such as alkanols, e.g., methanol, ethanol and isopropanol; glycols, e.g., ethylene glycol and propylene glycol; and polyols such as glycerine and glucose. In particular, the yield of the new polysaccharides in accordance with this invention is especially high when methanol is used as carbon source. The amount of carbon source is not critical as in any fermentation process and will be determined by the extent of growth or organism desired as well as the concentration of polysaccharide desired for processing from the final fermentation broth. Usually, the amount of the carbon source, especially methanol, can range up to about 5% by weight in the fermentation medium with from about 0.3 to about 3% by weight preferred to provide good bacterial growth and propagation.

As nitrogen source, inorganic nitrogen compounds normally employed in fermentation processes can be used, for example, ammonium sulfate, ammonium chloride, ammonia, diammonium phosphate, ammonium nitrate and sodium nitrate. Organic nitrogen sources can also be employed alone or in combination with inorganic sources, for example, urea, corn steep liquor, casein, peptone, yeast extract and meat extract.

Mineral salts are also present in the fermentation medium, such as, for example, calcium salts, magnesium salts, potassium salts, phosphate salts, iron salts, manganese salts, zinc salts and copper salts. Bacterial growth promoters include soy bean protein hydrolysate, yeast extract, vitamins and amino acids.

Cultivation of the organism in the nutrient medium is aerobically carried out at a temperature in the range of from about 20° to about 42° C., preferably 25° to 38° C. and at a pH at or near neutral, usually from about 5 to about 9, preferably from 5.5 to 7.5 by means of shaken or submerged cultivation.

Table 1 shows an example of synthetic media containing methanol which can be used in this invention.

TABLE 1

| | |
|---|---|
| Methanol | 1.5 wt. % |
| Diammonium monohydrogen Phosphate | 0.40 wt. % |
| Monopotassium dihydrogen phosphate | 0.10 wt. % |
| Dipotassium monohydrogen phosphate | 0.10 wt. % |
| Magnesium sulfate heptahydrate | 0.05 wt. % |
| Ferrous sulfate heptahydrate | 0.001 wt. % |
| Calcium chloride dihydrate | 0.001 wt. % |
| Yeast extract | 0.02 wt. % |
| Water | Balance |
| pH | 7.0 |

During the cultivation the pH value of the culture may change to a lower value depending on the medium used. Alkali such as ammonia, sodium hydroxide or potassium hydroxide may be added for maintaining the pH at a predetermined value.

The polysaccharides of this invention have molecular weight which are distributing in a range of about $1 \times 10^4$ to about $1 \times 10^7$ as mentioned above. The molecular weight values may somewhat change depending on the conditions employed to cultivate the microorganism. For example, the concentration ratio of carbon sources and nitrogen sources, and the concentration of phosphates may affect the molecular weight of the polysaccharides, which may also somewhat change depending on the ratio of methanol and ammonia in methanolic-ammonia used to adjust the pH of the culture medium. The separation of the polysaccharides containing allose as a constituent sugar from the culture is carried out using standard procedures of which the following is representative. After the cultivation, the medium is subjected to a centrifugal separation, or filtration using a filter-aid, to remove the mature Pseudomonas cells. Crude polysaccharides are obtained from the filtered medium as white fibers by the addition of a water soluble organic solvent such as acetone, methanol, ethanol or the like. For purification, the crude polysaccharides can be dissolved in water, after washing with ether and ethanol and heat-drying such as at 80° C. for 15 minutes, and the aqueous solution treated with trichloroacetic acid to remove protein followed by centrifugation or filtration to remove precipitates. The resulting supernatant can then be subjected to a dialysis and lyophilization to give purified polysaccharides which can then be precipitated by addition of water-soluble organic solvents. Of course, it is not necessary to separate the polysaccharide into dry solid, since it can be used in the form of an aqueous solution.

Pseudomonas viscogena can produce the polysaccharides of this invention which contain allose as a constituent sugar in a high concentration and with a very high rate of the utilization efficiency for the carbon source. For example, it is possible to produce the polysaccharides in an amount of about 30 g/l based on the culture medium when the cultivation is carried out in a submerged culture using methanol as carbon source. It is also possible to obtain about 30° yield of polysaccharide based on the amount of methanol used.

Structural and physico-chemical characteristics of the new polysaccharide of this invention are as follows:
(1) Constituent sugars and their existence ratio (mole %)
  Allose: from about 6 to about 12

Galactose: from about 50 to about 60
Glucose: from about 10 to about 20
Mannose: from about 7 to about 14
Glucuronic Acid from about 10 to about 12

However, because linkages between manose and glucronic acid are relatively resistant to hydrolysis, the analytical value of mannose can be lower depending on the analytical method employed.

(2) Elementary analyses

Near values to those calculated from the general formula of $C_nH_{2n}O_n$ are given.

(3) Melting point

The polysaccharide shows no clear melting point, and is decomposed above the temperature of about 210°–220° C.

(4) Infra-red spectra

The spectra shows absorptions as mentioned below;
vicinity of 3,400 cm$^{-1}$ O—H stretching
vicinity of 2,890 cm$^{-1}$ C—H stretching
vicinity of 1,620 cm$^{-1}$ stretching of carboxylate anions
vicinity of 880 cm$^{-1}$ due to the orientation of β-glucosido linkages (5) Ultraviolet absorption spectra The spectra shows no distinct characteristic absorption.

(6) $^{13}$C Nuclear magnetic resonance spectra

A methyl signal of acetyl groups and a carboxyl signal in the carbonyl absorption domain were observed. However, a carbonyl signal of acetyl groups could not be confirmed. Accordingly, it is assumed that although a part of hydroxyl groups are acetylated, the ratio for the acetylation is considerably small.

(7) Solubility in solvent

The polysaccharides are soluble in water but insoluble in methanol, ethanol, ethers, acetone or the like.

(8) Color reaction

Anthrone reaction: positive
Ninhydrin reaction: negative
Dishce's Carbazole reaction: positive
Dische's Cysteine-sulfuric acid reaction: positive (9) Acidity Acidic

(10) Appearance

It shows white cotton-like or fibrous appearance in dry state.

(11) Molecular weight

Between about $1 \times 10^4$ and about $1 \times 10^7$

(12) Specific rotation $[\alpha]_D^{25}$ = about +30° to about +35°
(c=1, water)

(13) Appearance of aqueous solution

An aqueous solution of the polysaccharide is colorless and transparent and viscous.

(14) Attitude toward calcium salts

The polysaccharide is aggregated to gel in an alkaline aqueous solution when calcium hydroxide or a calcium salt such as calcium chloride is added to the solution.

Figure 1:
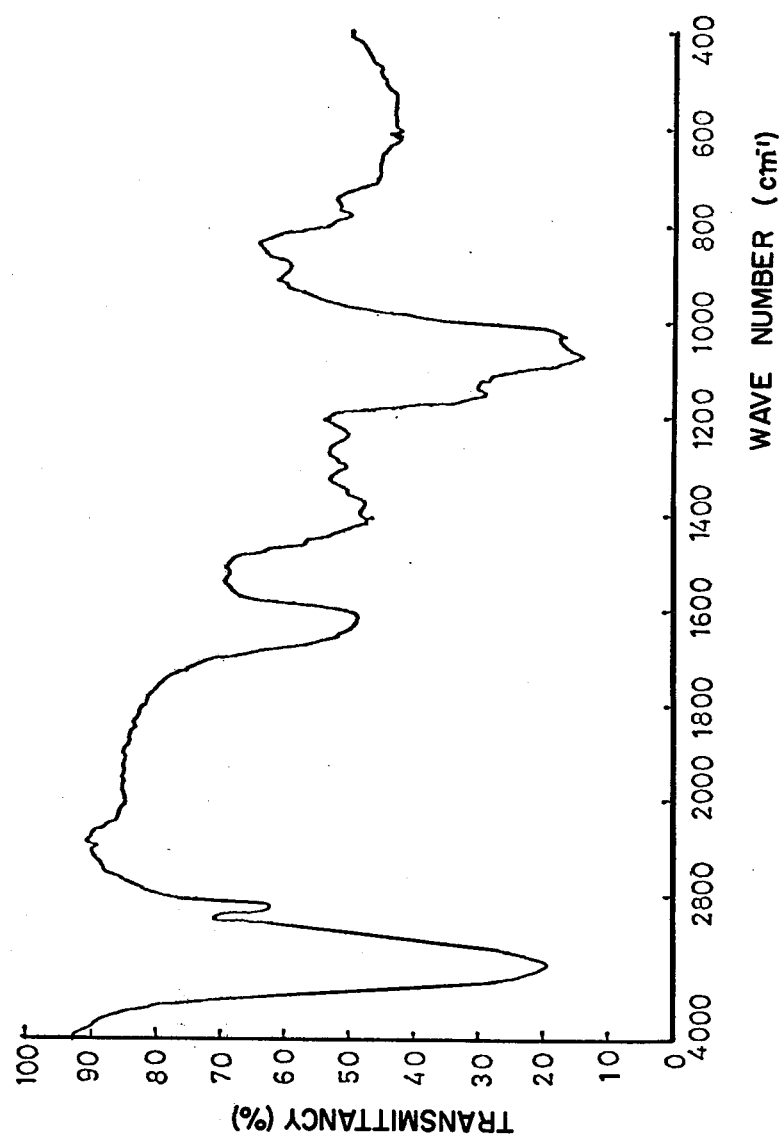
FIGS. 1 and 2 show the infra-red and ultraviolet spectra, respectively, of the new polysaccharides of this invention.

This invention is further illustrated by the following Examples.

EXAMPLE 1

1.0 liter of a solution having the same composition as shown in Table 1 except excluding methanol was charged into a 2.0 liters fermentation vessel of mini-jar type. After the vessel was sterilized at 120° C. for 15 minutes, 20 ml of methanol was introduced into the vessel under sterile conditions.

50 ml of a seed culture which was prepared by cultivating Pseudomonas viscogena TS-1004 strain in a medium having the same composition as the above prepared medium at 30° C. for 24 hours was inoculated into the vessel. Cultivation was carried out at 30° C. for 48 hours by means of submerged culture being stirred at 800 rpm while being aerated at the rate of 1 liter per minute during which ammonia water containing methanol was added to maintain the culture at pH 7.0.

The molar ratio of methanol and ammonia in the ammonia water containing methanol was 10:1. The total amount of methanol added to this culture during the cultivation was 73 g.

After the cultivation a double volume of water was added to the culture and the culture centrifuged at 5° C., 10,000 rpm for 30 minutes to remove bacterial cells and solid materials. The resulting supernatant was poured into 3 volumes of acetone with agitation. The acetone-insoluble product was filtered and sufficiently washed with ethanol and ether and lyophilized to obtain 15.3 g of crude polysaccharide.

The crude polysaccharide (10 g.) was dissolved again in water and trichloroacetic acid was added to reach a concentration of 3 weight %. After standing overnight, the solution was centrifuged at 5° C., 10,000 rpm for 20 minutes to remove solid materials.

The supernatant was again poured into three volumes of acetone to precipitate the polysaccharide.

The resulting polysaccharide was again dissolved in water and an aqueous solution of cetyl trimethyl ammonium bromide was added to the solution to precipitate the polysaccharide as a complex with cetyl trimethyl ammonium bromide. The complex was sufficiently washed with water and ethanol to remove excess cetyl trimethyl ammonium bromide and then dissolved in an aqueous solution of sodium chloride. Into this solution three volumes of ethanol were added to precipitate the polysaccharide, which was separated, lyophilized and again dissolved in water. The resulting solution was charged in a cellophane tube for dialysis and dialyzed in flowing water for 3 days. Then three volumes of acetone were added to the solution for the precipitation of the purified polysaccharide (yield=8 g.).

Results of elementary analysis of the resulting purified polysaccharide are as follows:

Elementary analysis

|   | Found (%) | Calculated value (%) from $C_nH_{2n}O_n$ |
|---|---|---|
| C | 40.25 | 40.00 |
| H | 6.06 | 6.67 |
| O | 53.02 | 53.33 |
| N | 0.67 | |

Melting point

The polysaccharide showed no clear melting point. Weight loss initiating from temperatures of 210° to 220° C., which was accompanied with exothermic heat was observed in a differential thermal balance provided with a recorder at the rate of 10° C./minute for rising temperature in the presence of air.

Infra-red absorption

Spectrum given by means of KBr tablet is shown in FIG. 1.

Ultra-violet absorption

Figure 2:
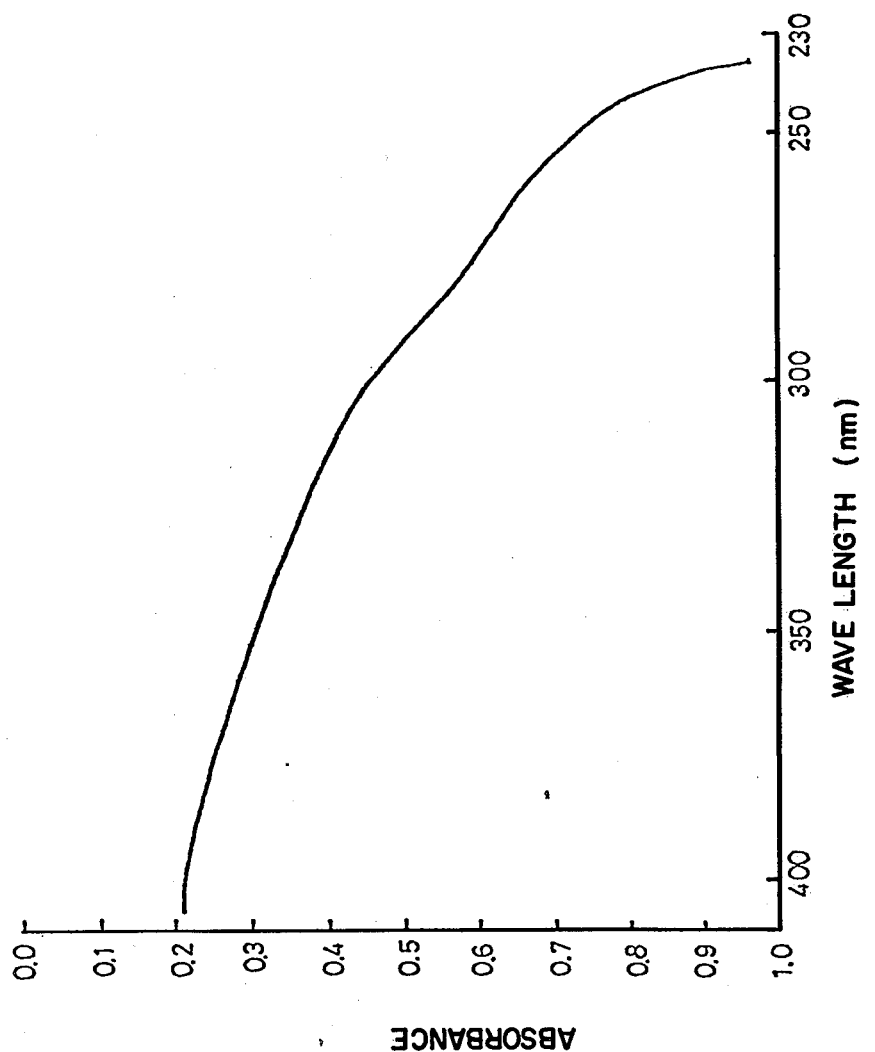

Ultra-violet absorption spectrum observed in an aqueous solution in which the concentration of the polysaccharide was 0.097% by weight, is shown in FIG. 2. From the Figure it can be seen that the spectrum has no clear characteristic absorption but the absorption increases somewhat below 310 nm and below 250 nm.

$^{13}$C Nuclear magnetic resonance absorption spectra

Signals due to chemical shifts were observed at 27.15 ppm and 176.97 ppm in δ value in a heavy water solution. They can be attributed to $^{13}$C of methyl groups in acetyl groups and of carbonyl group in carboxylic groups. However, the carbonyl signal of acetyl groups expected in the vicinity of 169.0 ppm in δ value was not found. Accordingly, it was assumed that although a part of hydroxyl groups are acetylated, the ratio for the acetylation is small.

Appearance, solubility and color reaction

The same characteristics and reactions as hereinbefore described were observed.

Molecular weight

It distributed between $1.0 \times 10^5$ and $5 \times 10^6$. The peak of the distribution was in $2 \times 10^6$.

The measurement was conducted by means of a gel permeation chromatography of a solution of the polysaccharide. The conditions were as follows:
 Amount of sample; 100 μl
 Column; 0.96 cm×60 cm
 Packing material; hydrophilic gel
 Eluent; a mixture solution of M/15 KH$_2$PO$_4$, M/15 Na$_2$HPO$_4$ and M/10 KCl
 Detector; differential refractometer
 Standard; dextran

Specific rotation

+32.2° (c=1, water)

Appearance of aqueous solution; acidity; and Attitude toward calcium salts

Aqueous solution of the polysaccharide was colorless and transparent. The solution showed a viscosity of 180 centipoises at room temperature when measured by a rotational viscometer. Addition of an aqueous solution of trimethyl ammonium bromide into the solution resulted in a white precipitate.

A white precipitate was also obtained by the addition of a solution of cetyl pyridinium chloride. Accordingly, the polysaccharide was acidic.

Addition of a calcium chloride aqueous solution into an aqueous solution of the polysaccharide which was adjusted to pH 10 by the addition of a sodium hydroxide resulted in aggregation to a gel.

Addition of aqueous calcium hydroxide gave the same result.

Constituent sugars; acidity; and chemical structure 10 mg of the purified polysaccharide was dissolved in 0.5 ml of sulfuric acid (2 N) and heated in a closed tube at 100° C. for 8 hours for the hydrolysis. The resulting hydrolysis solution was neutralized by barium carbonate and filtered. The filtrate was subjected to thin layer chromatography. The filtrate was spotted on a silica gel plate and developed by using developing solvent system of n-butanol, pyridine and water (volume ratio being 6:4:3). Then, water-saturated n-butanol containing p-anisidine hydrochloride in an amount of 3% was sprayed and the plate heated at 110°–120° C. The presence of allose, galactose, glucose, mannose and glucuronic acid was observed.

For the quantitative determination of neutral sugars, the filtrate was passed through a column packed with a strongly acidic cation exchange resin in H$^+$-form and the column was washed with water. The passing solution was condensed.

Alditol acetylation followed by gas-chromatography was carried out on the condensed solution according to the method described in "General Polysaccharide Chemistry" edited by Harada and Koizumi, published by Kodansha, (1974) at page 68 as follows: 1 ml of the condensed solution was left standing overnight after the addition of 10 mg of sodium borohydride. Into the solution an excess amount of a strongly acidic cation exchange resin in H$^+$-form was added and the mixture was vigorously shaken for several minutes to decompose the excess amount of sodium borohydride. After filtration, the filtrate was dried in vacuum. Methanol was added to the resulting dried product which was again dried in vacuum at room temperature. Then, the addition of methanol and the drying in vacuum were repeated 10 times.

Acetylation was carried out by adding 0.2 ml of a solution of pyridine and acetic anhydride, (1:1 volume), and by heating at 100° C. for 2 hours. After cooling, a small amount of water was added to the reaction product and it was dried in vacuum at room temperature.

The addition of water and the drying in vacuum were repeated 4 times. The remaining product was dissolved in a small amount of chloroform and the resulting solution was used as the sample of the gas chromatography. The conditions were as follows:
 Column; 0.4 cm×200 cm glass column
 Packing material; 3% ECNSS-M supported on a diatomaceous earth treated with DMCS (100–120 mesh)
 Temperature of column; 190° C.
 Temperature at the entrance; 240° C.
 Carrier; nitrogen 40 ml/min.
 Detector; hydrogen ion flame-type Identification of the glucuronic acid was carried out as follows: 7.0 g of the purified polysaccharide was dissolved in 900 ml of sulfuric acid (2 N) and heated in boiling water for 8 hours for the hydrolysis. The resulting hydrolysis solution was neutralized by barium carbonate and filtered. The filtrate was passed through a column of 2.0 cm×13 cm packed with a strongly acidic cation exchange resin in H$^+$-form and the column was washed with water. The resulting passing solution was condensed to syrup. 5 g of the syrup was subjected to a column chromatography in which a cellulose column (CF-11, 4.1 cm, produced by Whatman), a mixture solution of n-butanol, pyridine and water in a volume ratio of 10:3:3 as the first eluent and ethanol and water (1:2 volume) as the second eluent were used. Elution conditions were 27 ml/hour and 17 ml per tube. Each fraction was subjected to a paper chromatography by descending process using paper (3 MM made by Whatman) and n-butanol, pyridine and water as the developing agent, to fractionate and isolate the fractions of mannose, glucose, galactose and glucuronic acid. The thus fractionated glucuronic acid fraction was dissolved in a small amount of water and an excess amount of sodium borohydride was added into the resulting solution which was then left standing at room temperature overnight. Into the solution was added an excess amount of strongly acidic cation exchange resin in $H^+$-form and the resulting mixture was vigorously shaken to decompose the excess of sodium borohydride. After filtration, the filtrate was dried in vacuum followed by the addition of methanol. The procedure of the methanol addition and drying was repeated 10 times. Then, the product was incorporated with a dry strongly acidic cation exchange resin in $H^+$-form and anhydrous methanol and heated at 100° C. for 2 hours. After cooling and filtering, water and sodium borohydride were added into the solution, which was then left standing overnight. Alditol acetylation and gas chromatography were carried out in the same way as in the above-mentioned alditol acetylation and gas chromatography of the neutral sugars. As a result it was determined that the uronic acid was glucuronic acid because only one peak corresponding to that of the acetylated alditol of glucose was observed.

Quantitative determination of glucuronic acid was carried out by carbasole-sulfuric acid method.

1.60 mg of the purified polysaccharide was dissolved in 0.50 ml of water and ice-cooled. Into the solution 3.0 ml of concentrated sulfuric acid was incorporated under cooling with ice and in keeping well agitation. The solution was heated in boiling water for 20 minutes and immediately cooled to room temperature by cold water. Into the solution 0.1 ml of 0.1% solution of carbasole prepared by dissolving 10 mg of carbasole into 10 ml of 95% alcohol was added. The amount of glucuronic acid was determined by measuring the absorbance at 535 mm after 2 hours from the addition of the carbasole solution.

Result showed that glucuronic acid was contained in the amount of 11.0 mole % in the purified polysaccharide.

From the value and the results of the above-mentioned gas chromatography analyses of the neutral sugars, it was found that the content of the constituent sugars in the purified polysaccharide was as follows:

Allose: 9.8 mole %
Galactose: 55.4 mole %
Glucose: 10.7 mole %
Mannose: 13.1 mole %
Glucuronic acid: 11.0 mole %

Allose identification and confirmation was not only by the coincidence of the retention time with that of an authentic sample in gas chromatography but also by the following:

The glucose fraction prepared by the above-mentioned column chromatography, followed by the paper chromatography, was subjected to electrophoresis using paper (3 MM made by Whatman) in a sodium borate solution (0.1 M, pH 9.2) and under an electric potential gradient of 15 V/cm gave 2 spots which were the same as those of authentic samples of glucose and allose, respectively. In addition, 40 mg of the glucose fraction was dissolved in 19.5 ml of a phosphate buffer solution (0.05 M, pH 6.8). Into the solution 1.5 ml of an aqueous solution of glucose oxidase (type V, prepared by Sigma Chemical Co., from *Aspergillus niger*) having a protein content of 5.7 mg/ml was added for the reaction. The reaction was continued at 37° C. for 10 hours. Then the reaction solution was heated to deactivate the enzyme and centrifuged to separate insoluble materials. The solution was deionized by a mixture of a strongly acidic cation exchange resin in $H^+$-form and a strongly basic anion exchange resin in $OH^-$-form and subjected to the paper chromatography under the above-mentioned conditions to isolate allose. Physical and chemical characteristics of the isolated allose coincided with those of an authentic sample of allose. It was seen that each constituent sugar was in D-form by the measurement of specific rotations of each isolated constituent sugar. It was also concluded from the methylation of the Hakomori method, Smith decomposition including relaxation hydrolysis, the infra-red spectrum and other properties that the main chain of the polysaccharide consisted of galactose coupled in $\beta$-1,3 linkages having side chains in the 4- and 6-positions, which side chains had galactose, mannose and glucose as well as glucuronic acid in the terminal positions.

10 ml of an aqueous solution of the purified polysaccharide (2% by weight) was added with 10 ml of an aqueous solution of calcium chloride (1.0% by weight) into 1 liter of a fermentation liquor obtained in a lysine fermentation which has 8.0 in pH and in a stage before removing microbial cells and the liquor was adjusted to pH 10. Then, the microbial cells settled out to leave a clear supernatant.

Thus treated liquor could very easily be filtered and L-lysine could be recovered from the filtrate. On the other hand, no substantial change was observed in the same fermentation liquor, when only the aqueous solution of calcium chloride was added to the liquor followed by the adjustment of pH as in the foregoing procedure. In the latter case, the liquor was not easily filtered as was the case with the untreated fermentation liquor. Substantially the same results were obtained with the crude polysaccharide instead of the purified polysaccharide.

EXAMPLE 2

The cultivation was carried out in a similar manner as in Example 1, using the medium which has the same composition as in Example 1 except using 0.005 weight % of ammonium sulfate, 0.005 weight % of ammonium chloride and 0.05 weight % of diammonium monohydrogen phosphate instead of 0.40 weight % of diammonium monohydrogen phosphate shown in Table 1 and excluding 0.02 weight % of yeast extract.

The cultivation was continued for 45 hours and 125 ml of ammonia water containing methanol was added for controlling pH value which had a methanol to ammonia molar ratio of 15:1.

The amount of the resulting crude polysaccharide prepared by the cultivation was 30.0 g. The crude polysaccharide was purified in the same manner as in Example 1 and purified polysaccharide which was substantially identical to that of Example 1 was obtained, as shown in the following results:

Elementary analysis

| | Found (%) | Calculated value from $C_nH_{2n}O_n$ (%) |
|---|---|---|
| C | 40.93 | 40.00 |
| H | 6.30 | 6.67 |
| O | 52.24 | 53.33 |

| | Found (%) | Calculated value from $C_nH_{2n}O_n$ (%) |
|---|---|---|
| N | 0.53 | — |

Molecular weight

It distributed between $1.0 \times 10^4$ and $1.0 \times 10^6$ and the peak of the distribution was in $2.0 \times 10^5$.

Specific rotation $[\alpha]_D^{25}; +31.9$ (c=1, water)

Composition of the constituent sugars

Allose: 6.2 mole %
Galactose: 52.4 mole %
Glucose: 17.8 mole %
Mannose: 12.5 mole %
Glucuronic acid: 11.0 mole %

The other characteristics were substantially the same as in Example 1.

EXAMPLE 3

1.0 liter of a solution having the same composition as shown in Table 1 except excluding methanol was charged into a 2.0 liter fermentation vessel of the mini-jar type. After the vessel was sterilized at 120° C. for 15 minutes, 20 ml of methanol was introduced into the vessel under sterile conditions. 50 ml of a seed culture which was prepared by cultivating Pseudomonas viscogena TS-1004 strain in a medium having the same composition as the above-prepared medium at 30° C. for 24 hours was inoculated into the vessel.

Cultivation was carried out at 30° C. for 16 hours by means of submerged culture while being stirred at 800 rpm and aerated at 1 liter per minute, during which sodium hydroxide (2 N) was added to maintain the culture at pH 7.0. Then a sufficient volume of the reaction medium was removed to leave 780 ml in the reactor, after which, new sterilized nutrient having the same composition except the concentration of methanol being 0.8% by weight was fed into the vessel at the rate of 135 ml/hour with simultaneous withdrawal of reaction medium at the same rate. A continuous flow cultivation was carried out in this way. The reaction medium removed after 45 hours from the initiation of the continuous cultivation contained microbial cells in an amount of 11.7 g/liter and the polysaccharide 17.1 g/liter.

The polysaccharide was recovered in the following manner. Into 200 ml of the extracted culture was added 400 ml of water and the mixture was centrifuged at 5° C., 10,000 rpm for 30 minutes to remove microbial cells and solids. The resulting supernatant was poured into 1.8 liter of acetone with agitation. Treatment of the mixture as in Example 1 gave 3.4 g of polysaccharide.

The resulting polysaccharide after purification was subjected to analysis in the same manner as in Example 1. Results are listed as follows:

Elementary analysis

| | Found (%) | Calculated value from $C_nH_{2n}O_n$ (%) |
|---|---|---|
| C | 39.67 | 40.00 |
| H | 6.41 | 6.67 |
| O | 53.20 | 53.33 |
| N | 0.72 | — |

Molecular weight

It distributed between $2.0 \times 10^4$ and $1.0 \times 10^6$ and the peak of the distribution was in $2.0 \times 10^5$.

Specific rotation $[\alpha]_D^{25}; +32.1°$ (c=1, water)

Composition of the constituent sugars

Allose: 10.9 mole %
Galactose: 59.3 mole %
Glucose: 11.0 mole %
Mannose: 7.5 mole %
Glucuronic acid: 11.3 mole %

The other characteristics were substantially the same as in Example 1.

EXAMPLE 4

The cultivation was carried out as in Example 1, using the medium which had the same composition as shown in Table 1 except having 0.20% by weight of ammonium sulfate, ammonium chloride and diammonium monohydrogen phosphate, respectively, instead of 0.40% by weight of diammonium monohydrogen phosphate. The cultivation time was 48 hours. 103 ml of ammonia water containing methanol (methanol and ammonia in the ratio of 10:1) was used to adjust the pH.

The resulting reaction liquor was treated in the same way as in Example 1 to give 19.8 g of a crude polysaccharide. Purification of the crude polysaccharide and the measurements and analyses of the resulting purified polysaccharide were carried out in the same way as in Example 1. The results are listed as follows:

Elementary analysis

| | Found (%) | Calculated value from $C_nH_{2n}O_n$ (%) |
|---|---|---|
| C | 40.12 | 40.00 |
| H | 6.35 | 6.67 |
| O | 53.08 | 53.33 |
| N | 0.45 | — |

Molecular weight

It distributed between $3.0 \times 10^4$ and $2 \times 10^6$ and the peak of the distribution was in $5.0 \times 10^5$.

Specific rotation $[\alpha]_D^{25}; +32.3°$ (c=1, water)

Composition of constituent sugars

Allose: 11.3 mole %
Galactose: 51.7 mole %
Glucose: 13.4 mole %
Mannose: 12.9 mole %
Glucuronic acid: 10.8 mole %

The other characteristics were substantially the same as in Example 1.

EXAMPLE 5

Cultivation and isolation of crude polysaccharide were carried out except employing the cultivation temperature at 27° C. and the cultivation time of 40 hours. The amount of the resulting crude polysaccharide was 12.5 g. Purification of the crude polysaccharide and the measurements and analyses of the resulting purified polysaccharide were carried out in the same way as in Example 1. Results are listed as follows:

Elementary analyses

|   | Found (%) | Calculated value from $C_nH_{2n}O_n$ (%) |
|---|---|---|
| C | 39.89 | 40.00 |
| H | 6.45 | 6.67 |
| O | 53.15 | 53.33 |
| N | 0.51 | |

Molecular weight

It distributed between $1.0 \times 10^4$ and $5.0 \times 10^5$ and the peak of the distribution was in $5.0 \times 10^5$.

Specific rotation $[\alpha]_D^{25}; +31.8°$ (c=1, water)

Composition of constituent sugars

Allose: 8.7 mole %
Galactose: 58.6 mole %
Glucose: 10.6 mole %
Mannose: 11.1 mole %
Glucuronic acid: 11.0 mole %

The other characteristics were substantially the same as in Example 1.

What is claimed is:

1. A polysaccharide containing allose as a constituent sugar, said polysaccharide having the following identifying characteristics:
   (a) a molecular weight ranging from about $1 \times 10^4$ to about $1 \times 10^7$;
   (b) no clear melting point;
   (c) a content of from about 6 to about 12 mole % allose, from about 50 to about 60 mole % galactose, from about 10 to about 20 mole % glucose, from about 7 to about 14 mole % mannose and from 10 to about 12 mole % glucuronic acid;
   (d) infra-red spectra showing O-H stretching in the vicinity of 3,400 $cm^{-1}$, C—H stretching in the vicinity of 2,890 $cm^{-1}$ and stretching of carboxylate anions in the vicinity of 1,620 $cm^{-1}$ due to the orientation of beta-glucosido linkages in the vicinity of 800 $cm^{-1}$;
   (e) no distinct characteristic ultraviolet absorption spectra;
   (f) solubility in water but insolubility in methanol, ethanol, ethers and acetone;
   (g) the following color reactions:
      anthrone reaction—positive
      ninhydrin reaction—negative
      Dische's carbazole reaction—positive
      Dische's cysteine-sulfuric acid reaction—positive;
   (h) a specific rotation in water $[\alpha]_D^{25}$ of from about +30° C.;
   (i) forms a colorless, transparent and viscous solution with water; and,
   (j) is aggregated to a gel in an aqueous solution containing calcium ion.

2. The polysaccharide according to claim 1, wherein the molecular weight ranges from about $1.0 \times 10^5$ to about $5 \times 10^6$.

3. The polysaccharide according to claim 1, wherein the molecular weight ranges from about $1.0 \times 10^4$ to about $1.0 \times 10^6$.

4. The polysaccharide according to claim 1, wherein the molecular weight ranges from about $2.0 \times 10^4$ to about $1.0 \times 10^6$.

5. The polysaccharide according to claim 1, wherein the molecular weight ranges from about $3.0 \times 10^4$ to about $2 \times 10^6$.

6. The polysaccharide according to claim 1, wherein the molecular weight ranges from about $1.0 \times 10^4$ to about $5 \times 10^5$.

* * * * *